(12) United States Patent
Fernandez et al.

(10) Patent No.: US 10,987,497 B2
(45) Date of Patent: Apr. 27, 2021

(54) BALLOON CATHETER WITH TACTILE FEEDBACK FEATURES AND REINFORCED LUMEN

(71) Applicant: Acclarent, Inc., Irvine, CA (US)

(72) Inventors: Carlos F. Fernandez, High Springs, FL (US); George L. Matlock, Pleasanton, CA (US); Gregory T. Douglass, Carlsbad, CA (US)

(73) Assignee: Acclarent, Inc., Irvine, CA (US)

( * ) Notice: Subject to any disclaimer, the term of this patent is extended or adjusted under 35 U.S.C. 154(b) by 184 days.

(21) Appl. No.: 15/971,476

(22) Filed: May 4, 2018

(65) Prior Publication Data

US 2018/0318565 A1 Nov. 8, 2018

Related U.S. Application Data

(62) Division of application No. 14/754,967, filed on Jun. 30, 2015, now Pat. No. 10,016,581.

(51) Int. Cl.
*A61M 29/02* (2006.01)
*A61M 25/00* (2006.01)
*A61M 25/06* (2006.01)
*A61M 25/10* (2013.01)

(52) U.S. Cl.
CPC ........ *A61M 29/02* (2013.01); *A61M 25/0068* (2013.01); *A61M 25/0662* (2013.01); *A61M 25/1025* (2013.01); *A61M 25/003* (2013.01); *A61M 2025/0681* (2013.01); *A61M 2025/1061* (2013.01); *A61M 2025/1084* (2013.01); *A61M 2029/025* (2013.01); *A61M 2210/0681* (2013.01)

(58) Field of Classification Search
CPC ............ A61M 29/02; A61M 2029/025; A61M 25/03; A61M 25/0662; A61M 25/1025; A61M 2025/0681; A61M 2210/0681; A61M 25/1027; A61M 25/1034; A61M 25/1036; A61M 25/104
See application file for complete search history.

(56) References Cited

U.S. PATENT DOCUMENTS

| 9,155,492 | B2 | 10/2015 | Jenkins et al. |
| 9,962,530 | B2 | 5/2018 | Johnson et al. |
| 10,016,581 | B2 | 7/2018 | Fernandez et al. |
| 2004/0267280 | A1* | 12/2004 | Nishide .................. A61F 2/958 606/108 |

(Continued)

*Primary Examiner* — Tuan V Nguyen
(74) *Attorney, Agent, or Firm* — Frost Brown Todd LLC

(57) ABSTRACT

A dilation apparatus includes a shaft, a dilation balloon, and a standoff member. The shaft includes a first lumen and a second lumen. The distal end of the second lumen is proximal to the distal end of the first lumen. The dilation balloon encompasses the second distal end of the second lumen such that the dilation balloon defines an interior in fluid communication with the second lumen. A distal portion of the standoff member is positioned within the interior of the dilation balloon. The distal portion of the standoff member is distal to the second distal end of the second lumen. The standoff member provides a pathway for fluid communication between the interior of the dilation balloon and the second lumen. The standoff member may include a tube, a thread, polymeric beading, or other structures.

19 Claims, 16 Drawing Sheets

(56) References Cited

U.S. PATENT DOCUMENTS

| | | |
|---|---|---|
| 2005/0187536 A1 | 8/2005 | Shelso et al. |
| 2006/0282147 A1 | 12/2006 | Andreas |
| 2007/0005092 A1* | 1/2007 | Godin .................. A61M 25/10 606/194 |
| 2007/0208373 A1* | 9/2007 | Zaver ....................... A61F 2/06 606/200 |
| 2008/0172084 A1* | 7/2008 | Kusleika .................. A61F 2/01 606/201 |
| 2008/0183128 A1 | 7/2008 | Morriss et al. |
| 2010/0030031 A1 | 2/2010 | Goldfarb et al. |
| 2010/0185145 A1* | 7/2010 | Pepper ................. B29C 66/112 604/103.1 |
| 2011/0004057 A1 | 1/2011 | Goldfarb et al. |
| 2011/0125132 A1 | 5/2011 | Krolik et al. |
| 2015/0224290 A1* | 8/2015 | Chanduszko ........... A61F 2/958 600/585 |

* cited by examiner

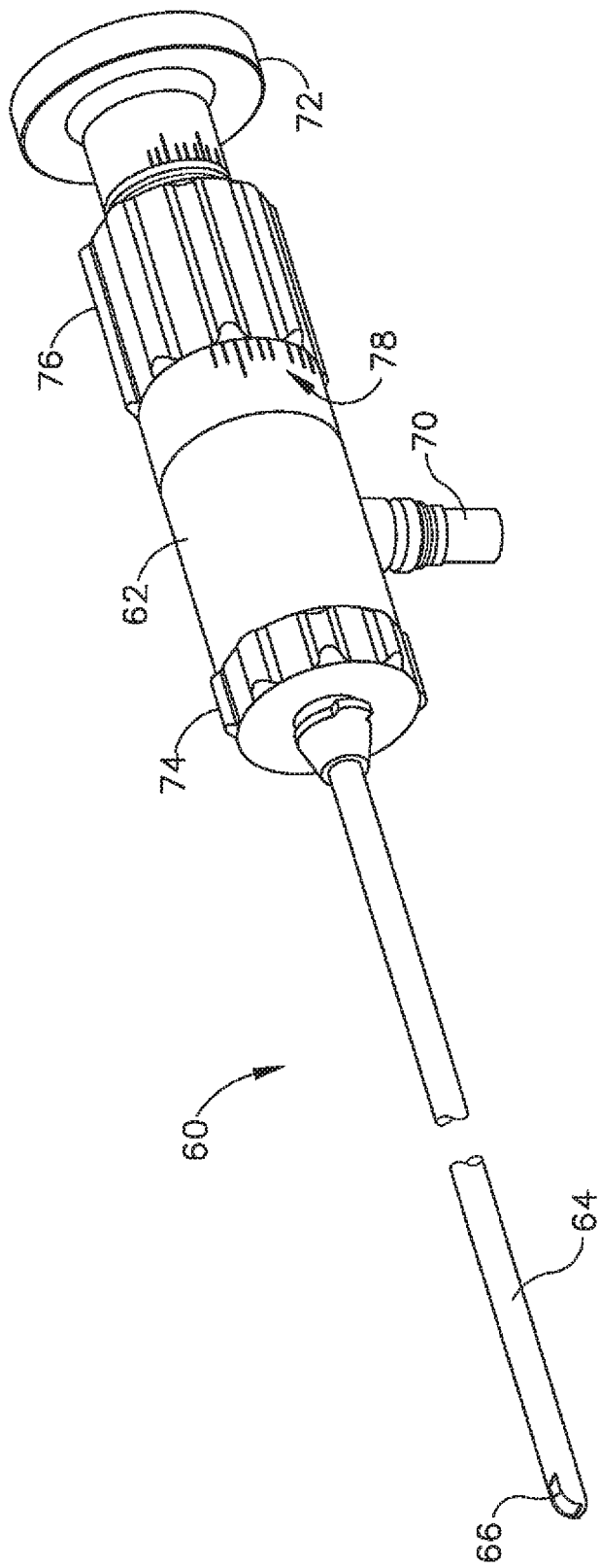
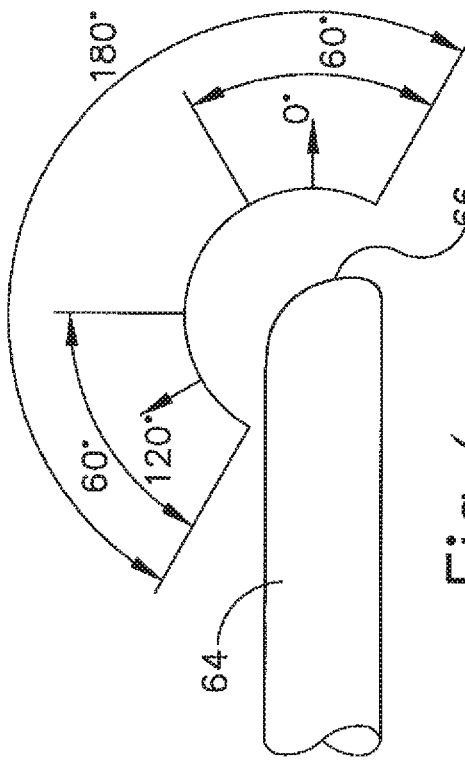
Fig. 5
Fig. 6

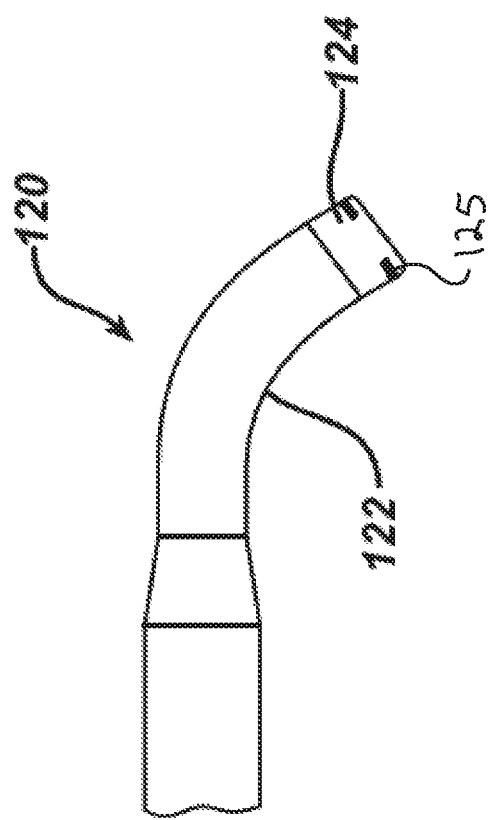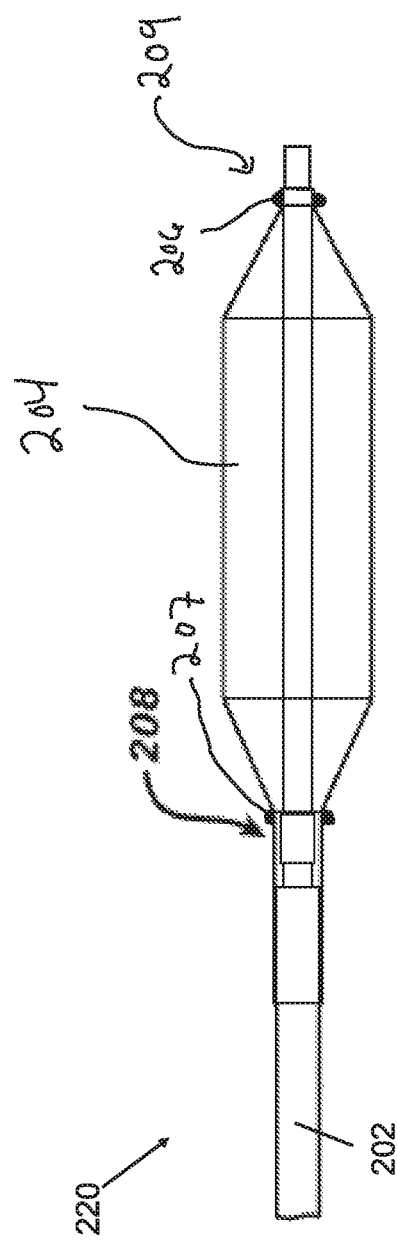

BALLOON CATHETER WITH TACTILE FEEDBACK FEATURES AND REINFORCED LUMEN

This application is a division of U.S. application Ser. No. 14/754,967, filed Jun. 30, 2015, entitled "Balloon Catheter with Tactile Feedback Features and Reinforced Lumen," issued as U.S. Pat. No. 10,016,581 on Jul. 10, 2018.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 depicts a perspective view of an exemplary endoscope suitable for use with the dilation catheter system of FIG. 1;

FIG. 6 depicts a side elevational view of the distal end of the endoscope of FIG. 5, showing an exemplary range of viewing angles;

FIG. 14 depicts a side elevational view of a distal portion of an exemplary alternative guide catheter that may be used with the dilation catheter system of FIG. 1;

FIG. 15 depicts a side elevational view of another exemplary alternative dilation catheter that may be used with the dilation catheter system of FIG. 1;

Figure 1:
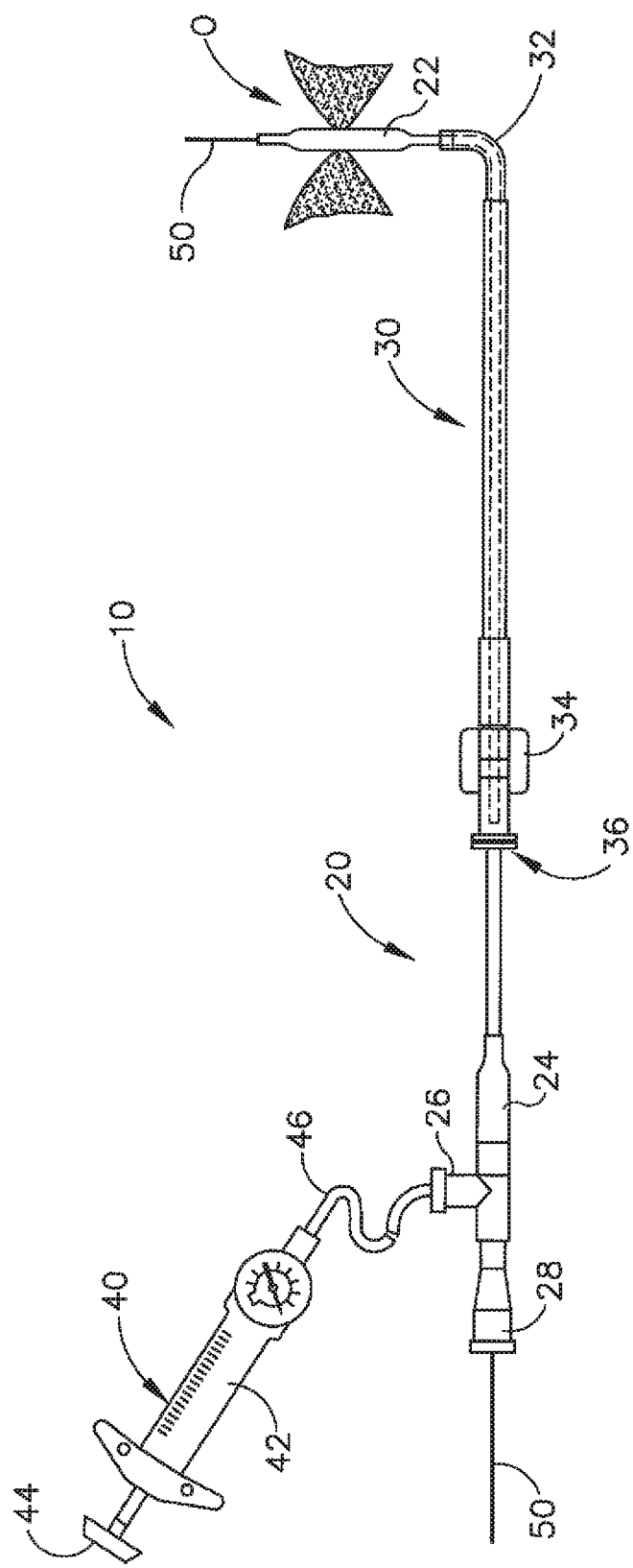
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
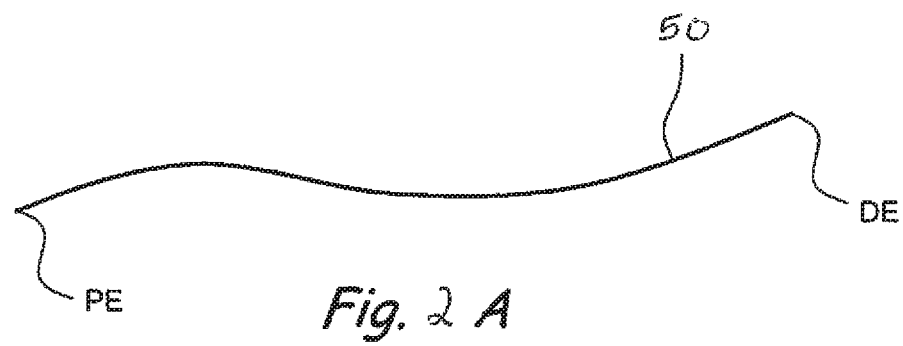
FIG. 2A depicts a side elevational view of an exemplary illuminating guidewire of the dilation catheter system of FIG. 1.
Figure 2B:
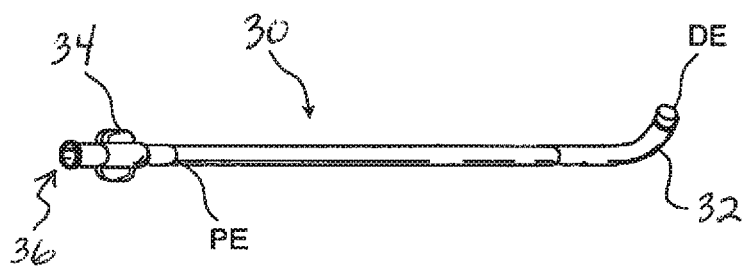
FIG. 2B depicts a side elevational view of an exemplary guide catheter of the dilation catheter system of FIG. 1.
Figure 2C:
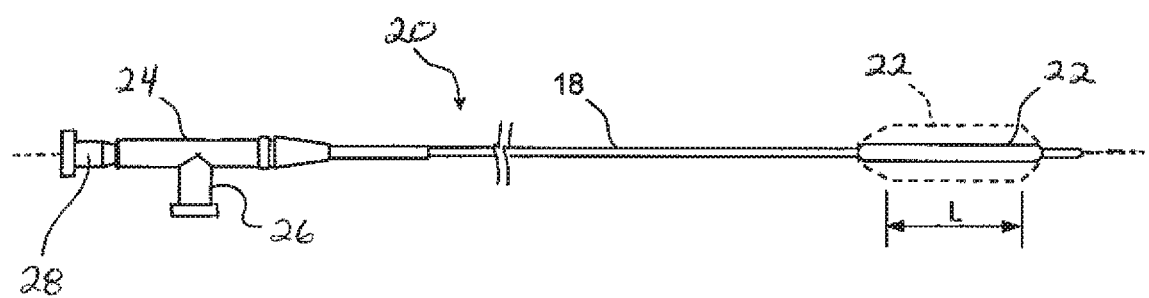
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, now U.S. Pat. No. 9,962,530, issued May 8, 2018, the disclosure of which is incorporated by reference herein.

Figure 3:
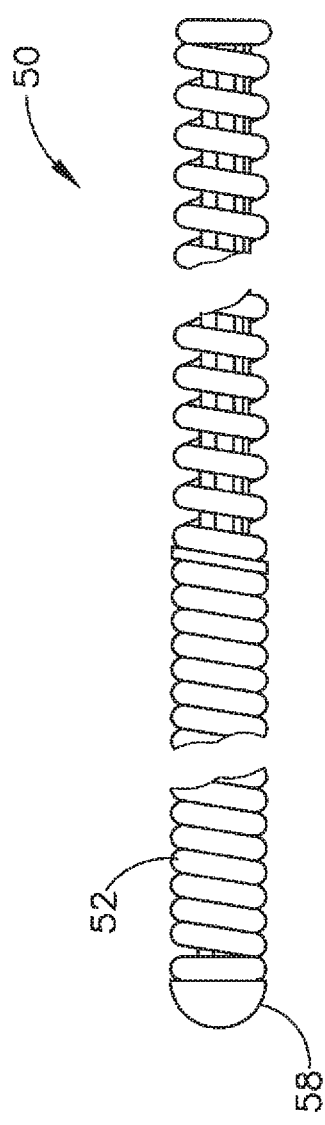
FIG. 3 depicts a detailed side elevational view of the illuminating guide wire of FIG. 2A.
Figure 4:
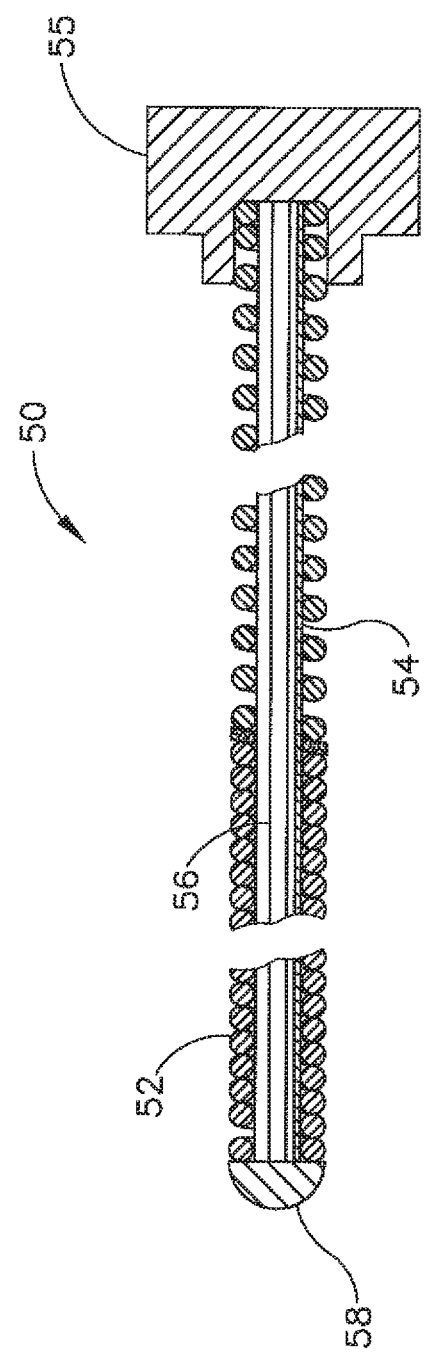
FIG. 4 depicts a detailed side cross-sectional view of the illuminating guidewire of FIG. 2A.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method for Dilating the Ostium of a Maxillary Sinus FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7:
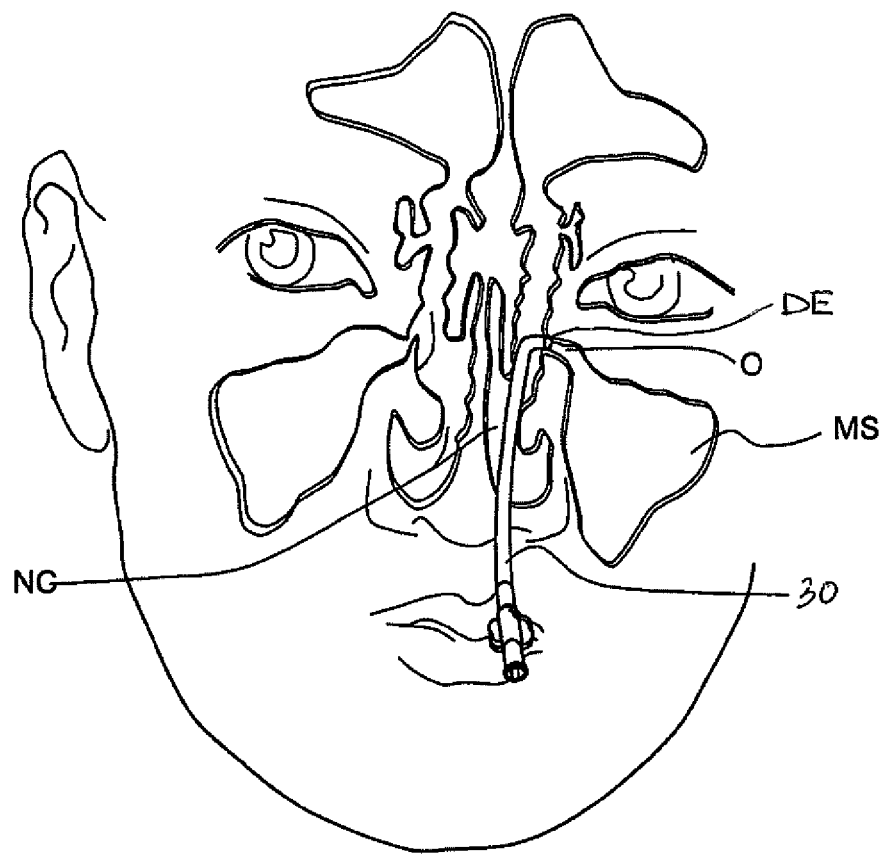
FIG. 7A depicts a front view of the guide catheter of FIG. 2B positioned adjacent an ostium of the maxillary sinus.
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.
FIG. 7E depicts a front view of an ostium of the maxillary sinus, with the ostium having been enlarged by inflation of the balloon of FIG. 7D.
Figure 7B:
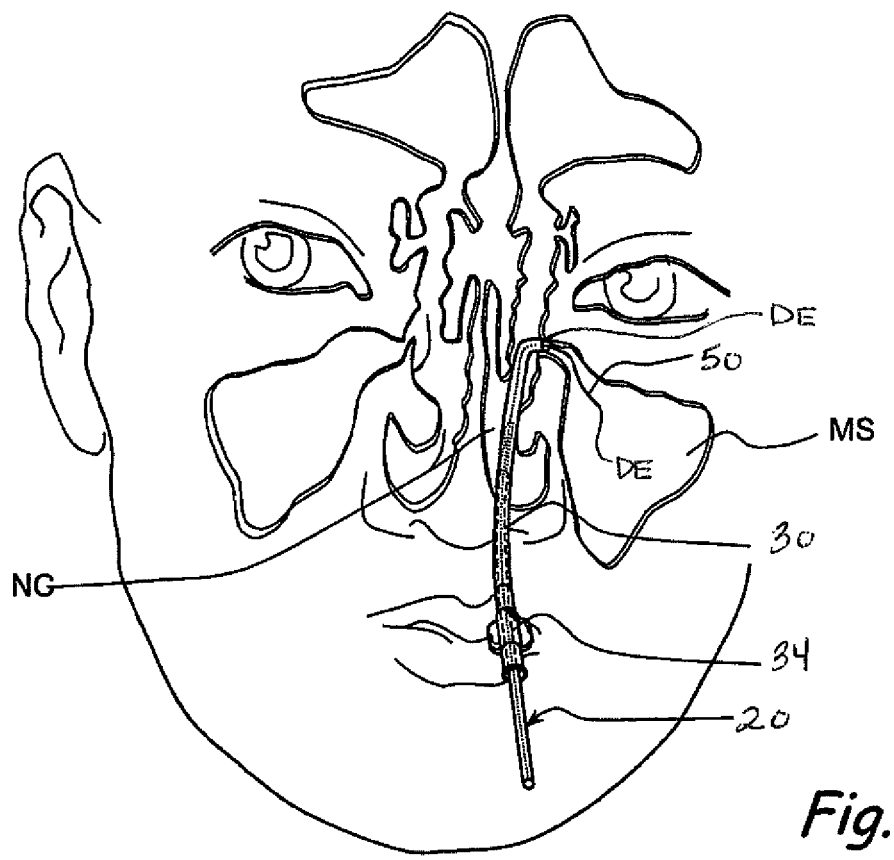
Figure 7C:
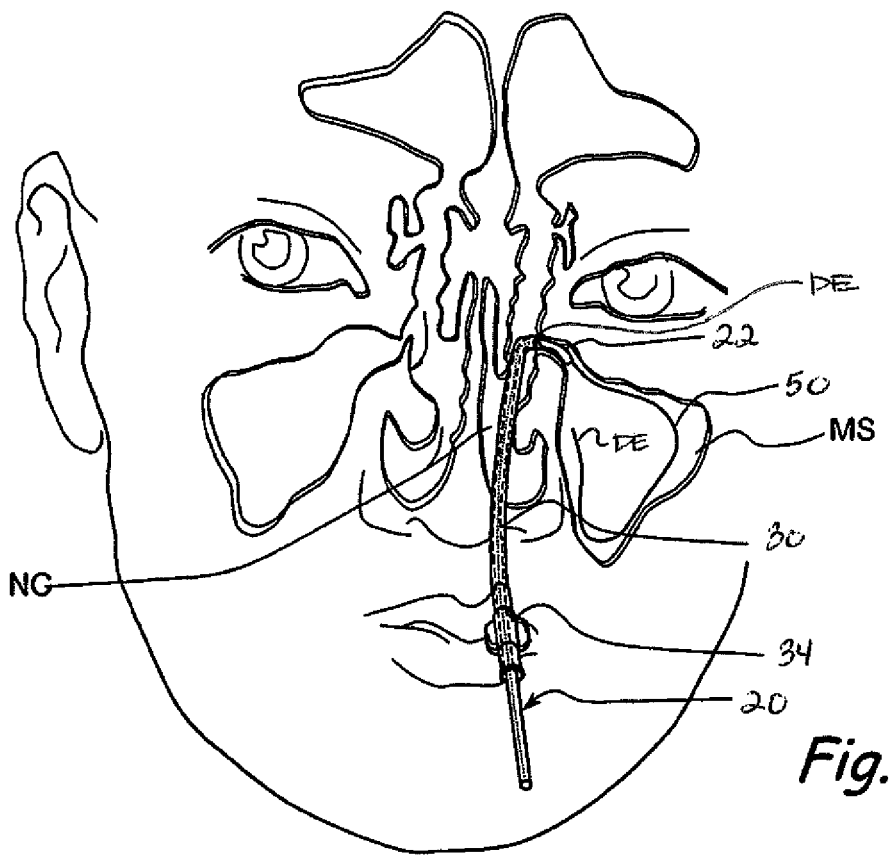

In the procedure of the present example, guide catheter (30) may be inserted. transnasally and advanced through the nasal cavity (NC) to a position within or near the targeted anatomical passageway to be dilated, the sinus ostium (0), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7D:
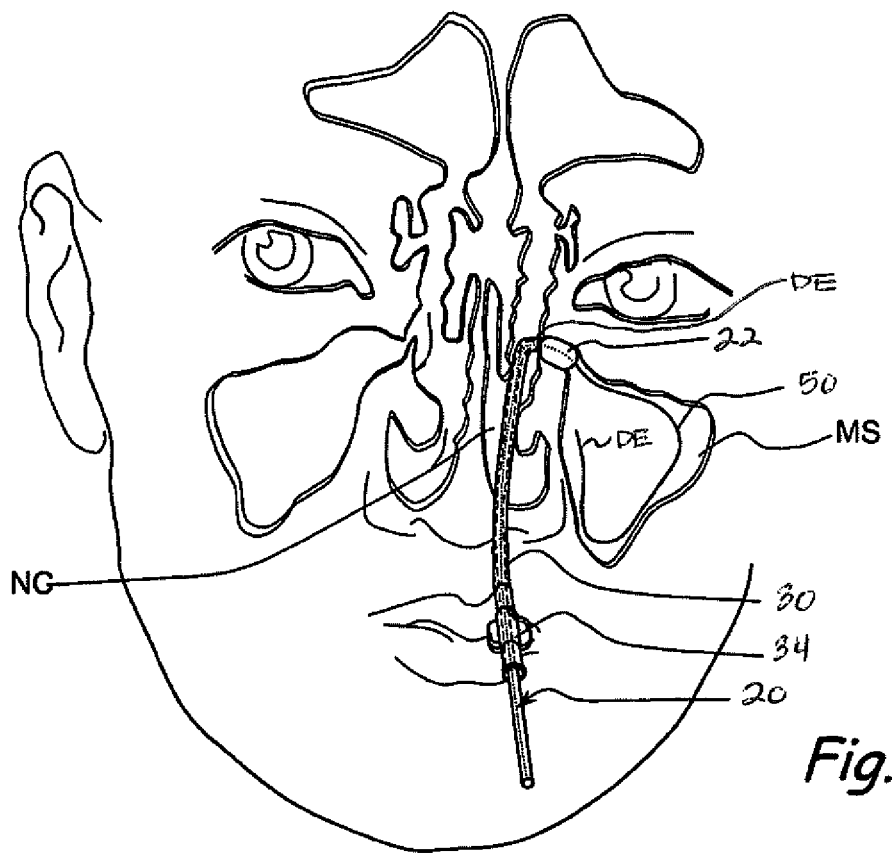
Figure 7E:
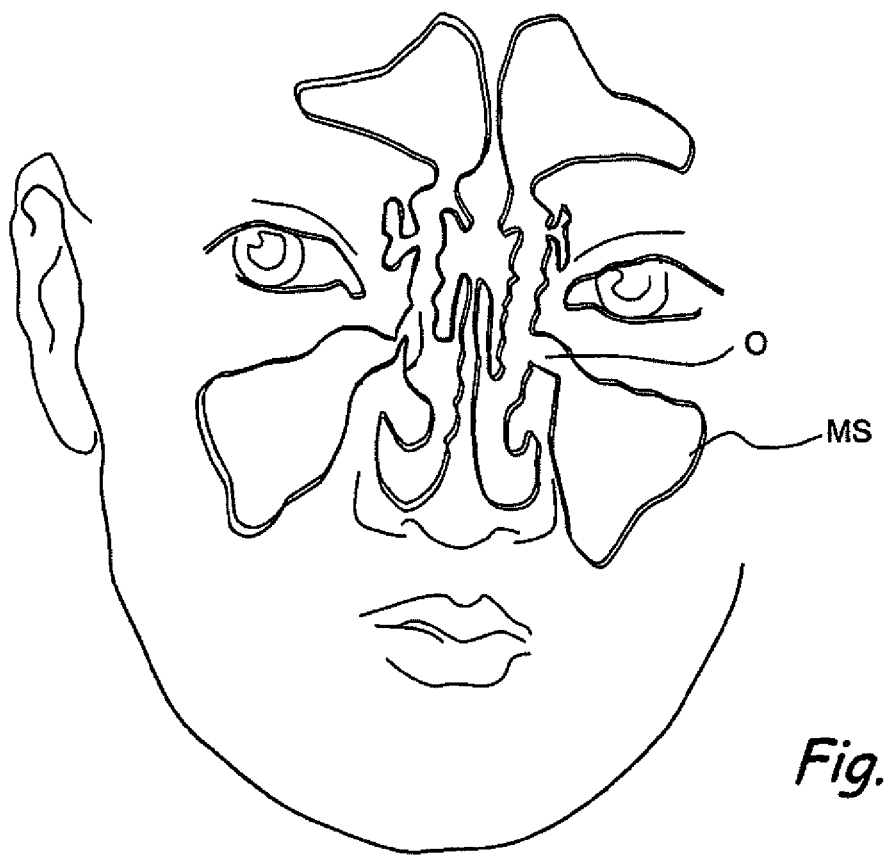

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (0). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pat. No. 7,630,676 Pub. No. 2008/0183128 entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Inflation Balloon with Internal Neck Support

In some instances, the inflation lumen of dilator catheter (20) may become partially or completely obstructed during deflation of inflatable dilator (22). For instance, the inflation lumen may become obstructed during the deflation process due to the negative pressure used to transport saline from inflatable dilator (22) back to inflator (40). The negative pressure used for deflation may retract the expandable region of inflatable dilator (22) back toward the inflation lumen, such that the material forming inflatable dilator (22) at least partially covers the fluid pathway between the inflation lumen and the interior of inflatable dilator (22). This retraction of the expandable region of inflatable dilator (22) may thus lead to an obstruction preventing communication of the saline within inflatable dilator (22) to inflator (40). If the inflation lumen becomes obstructed, deflation may occur too slowly or not at all. If inflation lumen is completely obstructed, an operator may have to lance and deflate inflatable dilator (22) externally. Therefore, it may be desirable to provide additional support between an inflation lumen of dilator catheter (20) and the expandable region of inflatable dilator (22). This additional support may help prevent obstruction of the inflation lumen, thereby leading to faster and more consistent deflation performance.

A. Exemplary Support Collar

Figure 8:
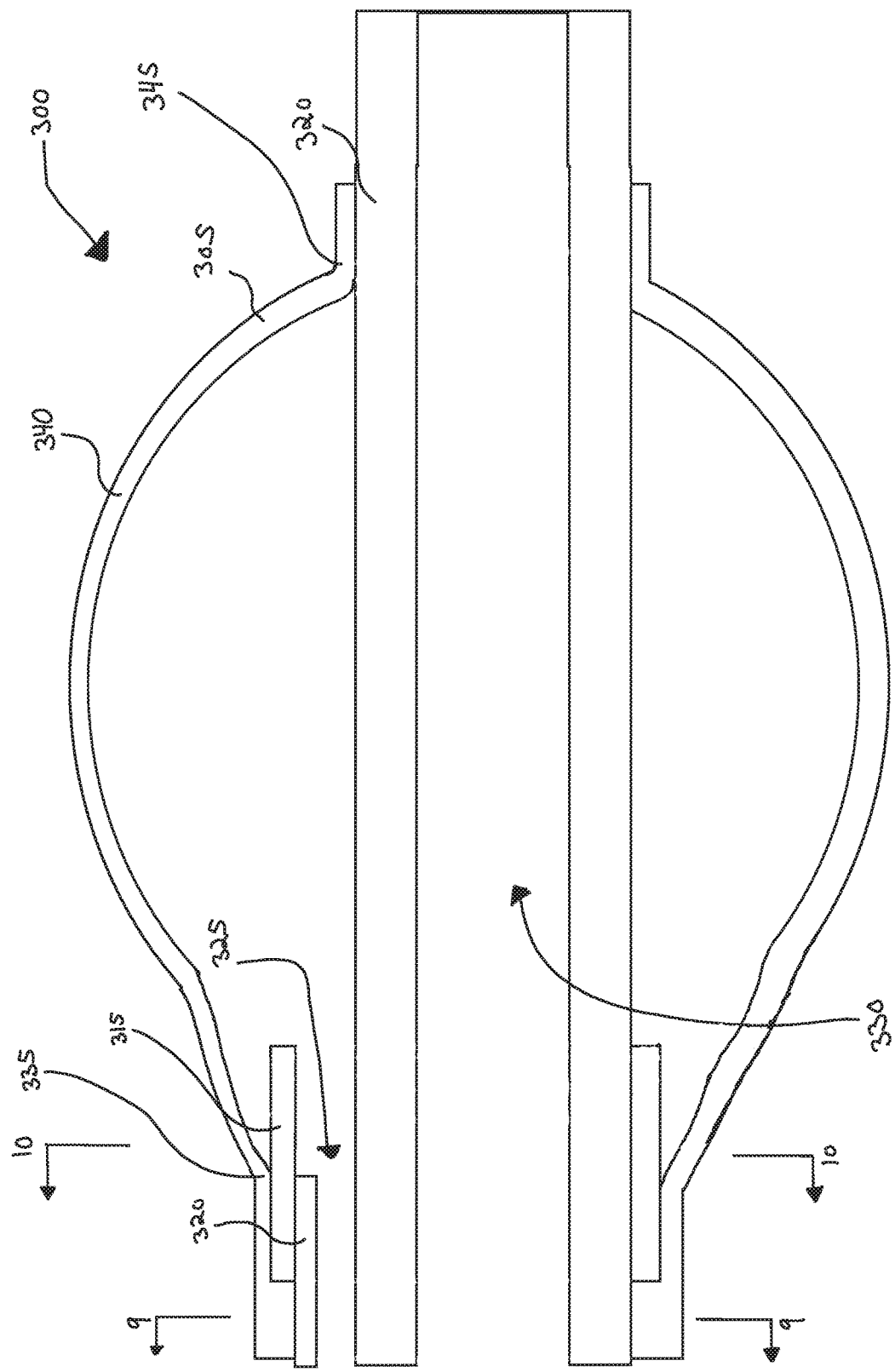
FIG. 8 depicts a side cross-sectional view of an exemplary alternative dilation catheter that may be used with the dilation catheter system of FIG. 1.
Figure 10:
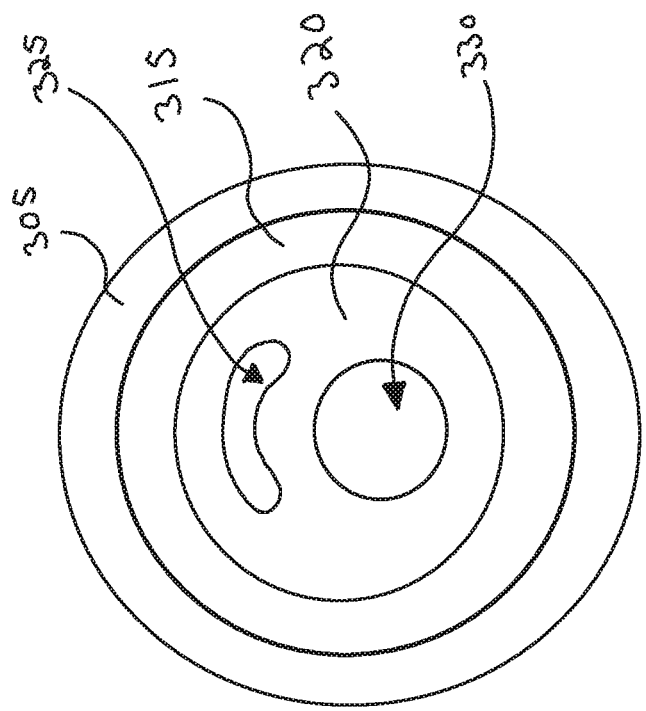
FIG. 10 depicts a front cross-sectional view of the dilation catheter of FIG. 8, taken along the 10-10 of FIG. 8.
Figure 9:
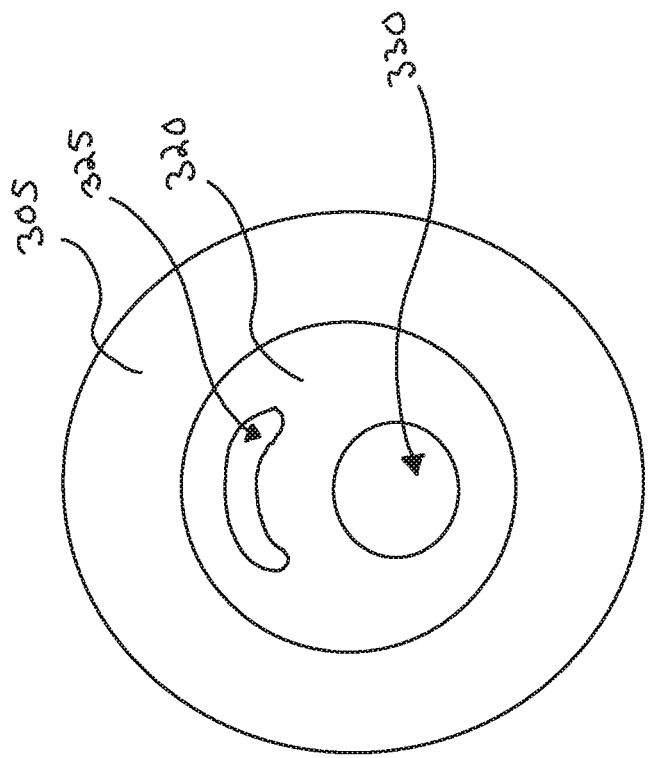
FIG. 9 depicts a front cross-sectional view of the dilation catheter of FIG. 8, taken along line 9-9 of FIG. 8.

FIG. 8 depicts an exemplary dilation catheter (300) that may be readily incorporated into dilation catheter system (10) in place of dilation catheter (20). Dilation catheter (300) comprises a hollow elongated shaft (320), a dilation balloon (305), and a support collar (315). Hollow elongated shaft (320) is substantially similar to hollow elongate shaft (18) mentioned above. As best seen in FIGS. 8-10, hollow elongated shaft (320) defines inflation lumen (325) and guidewire lumen (330). Inflation lumen (325) is substantially the same as the first lumen of dilation catheter (20) mentioned above. Inflation lumen (325) provides fluid communication between a fluid source (e.g., inflator (40), etc.) and the interior of dilation balloon (305). Guidewire lumen (330) is substantially the same as the second lumen of dilation catheter (20) mentioned above. Guidewire lumen (330) is configured to slidably receive guidewire (50). Inflation lumen (325) and guidewire lumen (330) are fluidly isolated from each other.

Dilation balloon (305) comprises a proximal neck region (335), an expandable region (340) and a distal neck region (345). Dilation balloon (305) encompasses a distal portion of hollow elongated shaft (320). Proximal neck region (335) is adhered to shaft (320) and collar (315). Distal neck region (345) is also adhered to shaft (320). Distal neck region (345) and proximal neck region (335) provide a fluid tight seal against the exterior surface of shaft (320) and collar (315), allowing expandable region (340) to inflate and deflate as fluid is communicated from and to inflation lumen (325). As mentioned above, expandable region (340) is configured to inflate to a volume, similar to that in FIG. 8 in response to pressurized fluid provided by inflator (40). Expandable region (340) is also configured to deflate in response to evacuation of fluid provided by inflator (40).

While hollow elongated shaft (320) defines both inflation lumen (325) and guidewire lumen (330) along most of the length of shaft (320), the distal-most portion of shaft (320) that defines inflation lumen (325) is cut out near the proximal neck region (335). In other words, inflation lumen (325) terminates prior to guidewire lumen (330), leaving an opening for inflation lumen (325) within dilation balloon (305). As best seen in FIGS. 8-10, support collar (315) is located near proximal neck region (335) to encompass the cut out of elongated shaft (320) defining the termination of inflation lumen (325). Support collar (315) extends distally past the termination of inflation lumen (325) to help ensure fluid communication between dilation balloon (305) and inflation lumen (325). It should also be noted that proximal neck region (335) is adhered to only a proximal portion of support collar (315) and not to a distal portion of support collar (315) in this example.

In particular, support collar (315) acts as a shield to prevent obstruction between inflation lumen (325) and dilation balloon (305) in at least two ways. First, because support collar (315) extends distally past the termination of inflation lumen (325), a larger cross-sectional area is provided for fluid communication between inflation lumen (325) and dilation balloon (305). In fact, the cross-sectional area provided increases from the size of inflation lumen (325) as shown in FIGS. 9-10, to the cross-sectional perimeter defined by the inner diameter of support collar (320) and the cutout of elongated shaft (320). An increase in cross-sectional may enhance fluid communication between dilation balloon (305) and inflation lumen (325), thereby preventing expandable region (340) from obstructing fluid communication when negative pressure is utilized to deflate dilation balloon (305).

Additionally, because support collar (315) extends into expandable region (340) of dilation balloon (305), and because proximal neck region (335) is not adhered to a distal portion of support collar (315), more surface area of expandable region (340) will have to come into contract with the outer diameter of support collar (315) as dilation balloon (305) deflates before dilation balloon (305) is able to obstruct fluid communication between inflation lumen (325) and dilation balloon (305). Therefore, not only does the increase in cross-sectional area provided by support collar (315) help prevent fluid obstruction, but the longitudinally extending surface area of support collar (315) also helps prevent fluid obstruction.

B. Exemplary Offset Tube Support

Figure 11:
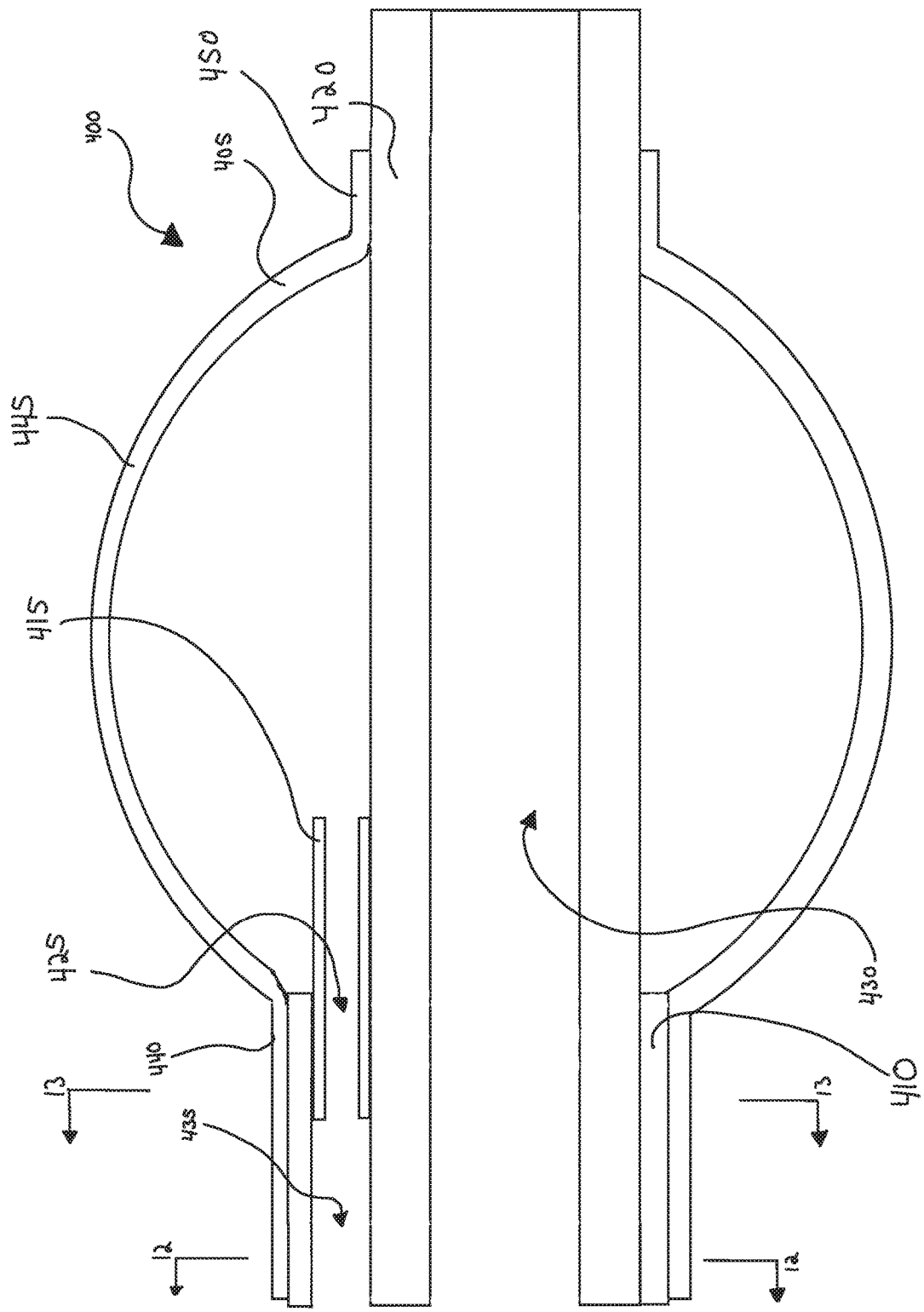
FIG. 11 depicts a side cross-sectional view of another exemplary alternative dilation catheter that may be used with the dilation catheter system of FIG. 1.
Figure 12:
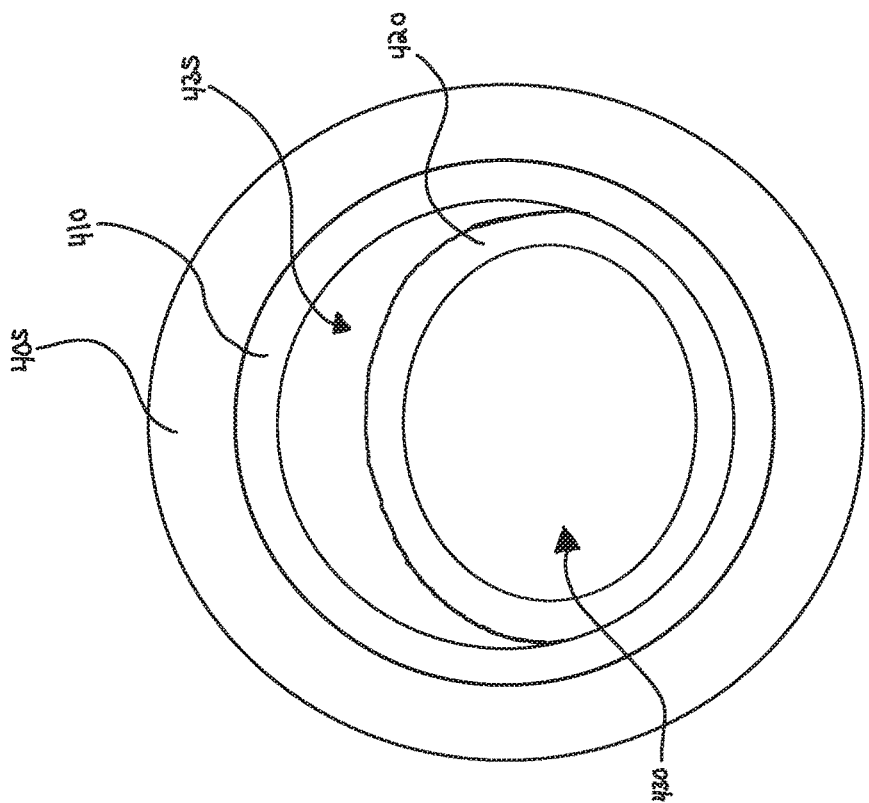
FIG. 12 depicts a front cross-sectional view of the dilation catheter of FIG. 11, taken along line 12-12 of FIG. 11.

FIG. 11 depicts another exemplary dilation catheter (400) that may be readily incorporated into dilation catheter system (10) in place of dilation catheter (20). Dilation catheter (400) comprises an outer tube (410), an inner tube (420), a dilation balloon (405), and an offset tube (415). Outer tube (410) and inner tube (420) combine together to perform substantially the same function as hollow elongated shaft (320) and hollow elongate shaft (18) mentioned above. Inner tube (420) defines guidewire lumen (430). Outer tube (410) and inner tube (420) are secured to one another and together define an inflation lumen (435), as best seen in FIG. 12. Inflation lumen (435) is substantially the same as the first lumen of dilation catheter (20) and inflation lumen (325) mentioned above. Inflation lumen (435) provides fluid communication between a fluid source and the interior of dilation balloon (405). Guidewire lumen (430) is substantially the same as the second lumen of dilation catheter (20) and guidewire lumen (330) mentioned above. Guidewire lumen (430) is configured to slidably receive guidewire (50). Inflation lumen (435) and guidewire lumen (430) are fluidly isolated from each other.

Outer tube (410) has a shorter length than inner tube (420), thereby creating an offset distance from the distal ends of outer tube (410) and inner tube (420). Since the combination of outer tube (410) and inner tube (420) define inflation lumen (435), inflation lumen (435) also terminates at the distal end of outer tube (410). Outer tube (410) terminates at a longitudinal position that is proximal to the longitudinal position at which inner tube (420) terminates, such that inflation lumen (435) terminates at a longitudinal position that is proximal to the longitudinal position at which guidewire lumen (430) terminates.

Dilation balloon (405) is substantially similar to dilation balloon (305). Dilation balloon (405) comprises a proximal neck region (440), an expandable region (445), and a distal neck region (450). Dilation balloon (405) encompasses a distal portion of outer tube (410) and a distal portion of inner tube (420). Proximal neck region (440) is adhered to outer tube (410). Distal neck region (450) is adhered to inner tube (420). Distal neck region (450) and proximal neck region (440) provide fluid tight seal against the exterior surface of inner tube (420) and outer tube (410) respectively, allowing expandable region (445) to inflate and deflate as fluid is communicated from and to inflation lumen (435). Similar to features of dilation balloon (305), expandable region (445) is configured to inflate to a volume, similar to that in FIG. 11, in response to pressurized fluid provided by inflator (40). Expandable region (445) is also configured to deflate in response to evacuation of fluid provided by inflator (40). It should be understood that proximal neck region (440) encompasses outer tube (410) and inner tube (420), while distal neck region (450) encompasses only inner tube (420).

Offset tube (415) may comprise a flexible material, or a material that is similar to that of outer tube (410) or inner tube (420), so that offset tube (415) does not increase rigidity and does not affect balloon insertion and retraction forces. In the present example, offset tube (415) is fixed within inflation lumen (435) by an interference fit between outer tube (410) and inner tube (420). However, offset tube (415) can be fixed within inflation lumen (435) by any other means known in the art. For example, offset tube (415) may be formed by part of the main balloon shaft and created by cutting away and leaving offset tube (415). Alternatively, offset tube (415) can be an added part that is attached prior to the balloon being assembled onto the balloon shaft using adhesives or a melt-boding process. It should be noted that dilation balloon (405) is not bonded to offset tube (415) in this example.

Offset tube (415) further defines a lumen (425) extending throughout offset tube (415). While in the present example, offset tube (415) defines lumen (425), lumen (425) is optional, and can be omitted if desired. In other words, offset tube (415) may be substituted with a solid rod or other structure, provided that such a solid rod (or other structure that lacks some kind of lumen) is configured to provide clearance between the interior of balloon (405) and inflation lumen (435). In some variations, offset tube (415) is replaced with a monofilament line, a multi-filament line, polymeric beading, and/or some other flexible structure that is configured to provide a standoff between the interior of balloon (405) inner tube (420), to thereby reduce or prevent the occurrence of inflation lumen (435) becoming occluded in the event that balloon (405) collapses against inner tube (420). Offset tube (415) extends distally outwardly from the distal end of inflation lumen (435), within dilation balloon (405). In other words, the proximal end of offset tube (415) is longitudinally positioned within inflation lumen (435) while the distal end of offset tube (415) is longitudinally positioned within dilation balloon (405). In some versions, the distal end of offset tube (415) is secured to inner tube (420), however this is entirely optional.

Figure 13:
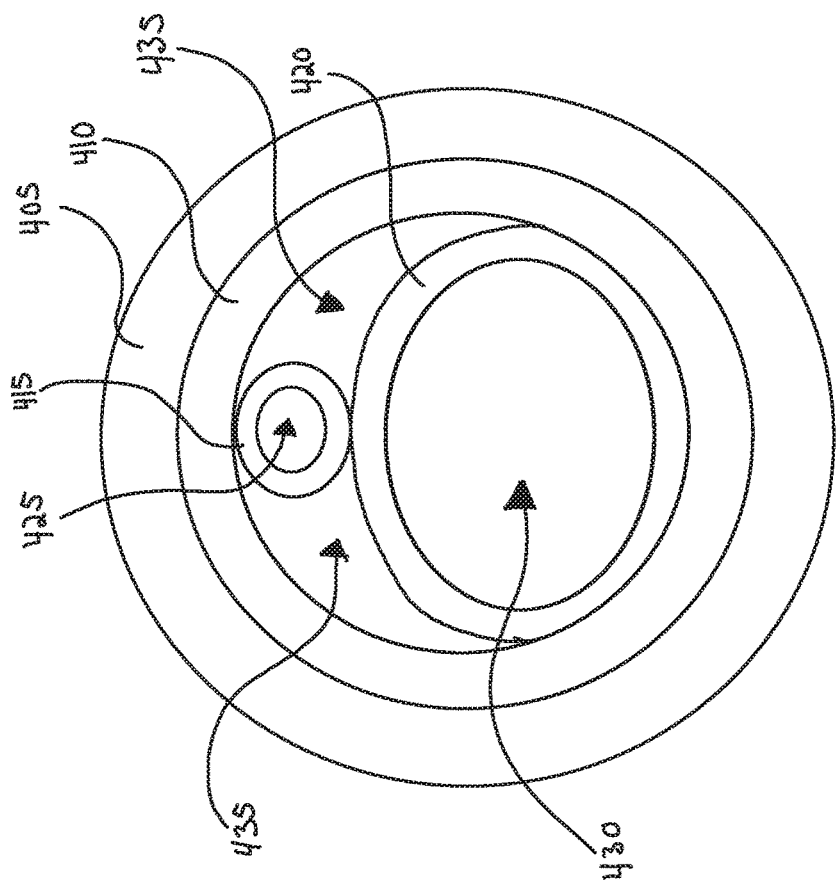
FIG. 13 depicts a front cross-sectional view of the dilation catheter of FIG. 11, taken along line 13-13 of FIG. 11.

Offset tube (415) is configured to help prevent expandable region (445) from obstructing fluid communication between dilation balloon (405) and inflation lumen (435), but in a different manner than support collar (315). As best seen in FIGS. 12-13, the presence of offset tube (415) does not increase the cross-sectional area of fluid communication between dilation balloon (405) and inflation lumen (435). However, extension of offset tube (415) into the interior of balloon (405) enables lumen (425) to act as an extended pathway for fluid communication between inflation lumen (435) and dilation balloon (405). As best seen in FIG. 13, offset tube (415) still leaves area for two separate inflation lumens (435) at the distal end of outer tube (410). Therefore, at the distal end of outer tube (410), there are two inflation lumens (435) separated by offset tube (415). Offset tube (415) thus effectively creates three paths for fluid communication between inflation lumen (435), such that if one path happens to become obstructed by a portion of balloon (405) during deflation of balloon (405) the other two paths may still be open. Since one of the fluid communication paths, (i.e., lumen (425)) is offset from the other two fluid communication paths, it may be less likely for all three pathways would to be obstructed to prevent deflation of balloon (405). It should also be understood that offset tube (415) may provide some degree of structural integrity to inflation lumen (435), reducing the risk that the distal end of inflation lumen (435) may become closed off due to kinking of dilation catheter (400).

V. Exemplary Indicator Delineating Longitudinal Position of Inflation Balloon

As mentioned above, in some instances an endoscope (60) may be used to provide visualization within an anatomical passageway during a procedure in which dilation catheter system (10) is used. Endoscopes (60) may allow an operator to utilize visual markers on dilation catheters (20) to indicate whether or not advancement of a dilation catheter (20) is complete. Additional markers may also be placed on the hollow elongated shaft (18), at a location proximal to the proximal end of guide catheter (30), to provide visual feedback indicating the longitudinal position of dilation catheter (20) in relation to guide catheter (30), which may further indicate whether inflatable dilator (22) has reached a proper location within the patient. However, in some situations, it may be difficult to visually determine whether or not a dilation catheter (20) has been advanced far enough, or advanced too far. Additionally, it may be difficult for an operator to confirm visual locations on markers located both within the endoscopic field of view and at a location proximal to the proximal end of guide catheter (30). Therefore, it may be desirable to provide tactile markers on both guide catheter and balloon catheter, which may provide the operator with tactile feedback to thereby provide clear confirmation of where dilation catheter (20) is in relation to guide catheter (30).

FIG. 14 shows a distal portion (120) of an exemplary guide catheter (100) that may be used in place of guide catheter (30) described above. Guide catheter (100) of this example comprises a bend (122) and a distal tip (124). Distal tip (124) further comprises a pair of tactile markers (125). Tactile markers (125) are in the form of inwardly projecting protrusions within the inner lumen of guide catheter (30), distal to bend (122). While two tactile markers (125) are used in the present example, any number of tactile markers (125) may be used as will be apparent to a person having ordinary skill in the art in view of the teachings herein. Tactile markers (125) are placed as far to the end of the distal tip (124) as possible in this example. The placement of tactile markers (25) in the present example signals to an operator when any object interacting with tactile markers (125) is either exiting or entering distal tip (124) of guide catheter (100). However, placement of tactile markers at the end of distal tip (124) is merely one option. Placement of tactile markers (125) along any other portion of guide catheter (100) may be utilized for a variety of purposes as will be apparent to a person having ordinary skill in the art in view of the teaching herein.

FIG. 15 shows a distal portion of an exemplary dilation catheter (220) that may be used in place of dilation catheter (20) described above. Dilation catheter (220) comprises an inflation balloon (204) having a proximal end (208) and a distal end (209) attached to a hollow elongated shaft (202). Dilation catheter (220) further comprises a set of tactile markers (207) on proximal end (208) of inflation balloon (204) and a set of tactile markers (206) on distal end (209) of inflation balloon (204). Tactile markers (206) are in the form of outwardly projecting protrusions. Tactile markers (206) are configured to interact with tactile markers (125) in a detent type of relationship, such that tactile markers (206, 125) will cause a slight and temporary interference as dilation catheter (220) is advanced and retracted relative to guide catheter (120). This slight and temporary interference may be felt by the hand of the operator grasping dilation catheter (220) and/or guide catheter (120) thereby providing tactile feedback. The placement of both sets of tactile markers (207, 206) thus enables the operator to feel when either distal end (209) of inflation balloon (204) or proximal end (208) of inflation balloon (204) is interacting with tactile markers (125) of guide catheter (120). In the present example, tactile markers (125, 206, 207) indicate when either distal end (209) or proximal end (208) of inflation balloon (204) is entering or exiting distal end of guide catheter (120).

Figure 16A:
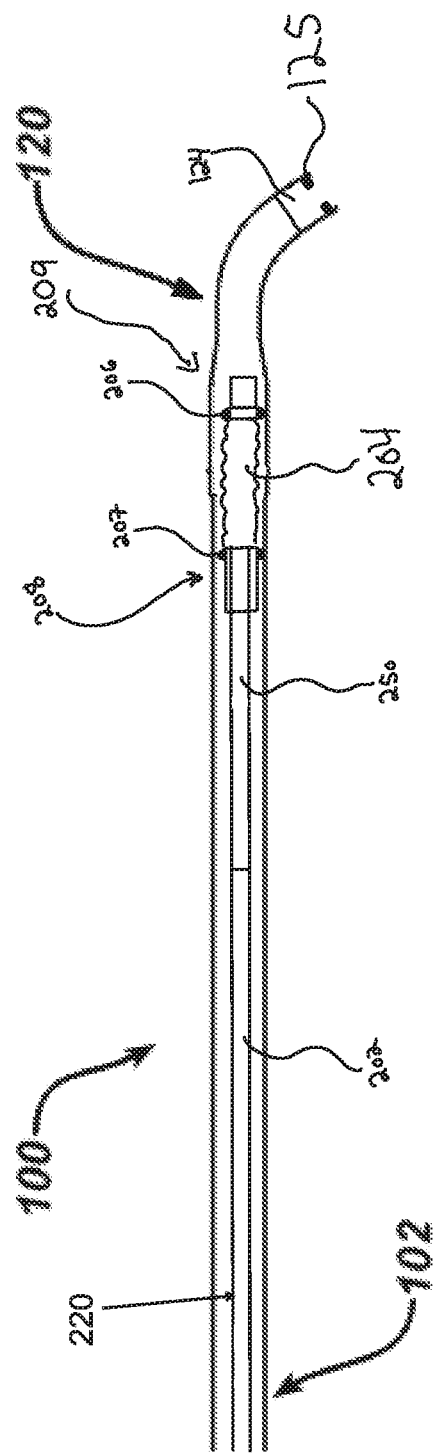
FIG. 16A depicts a side cross-sectional view of the dilation catheter of FIG. 15 disposed in the guide catheter of FIG. 14, with the dilation catheter in a proximal position, and with a balloon of the dilation catheter in a non-expanded state.

FIG. 16A-D show hollow elongated shaft (202) of dilation catheter (220) pushing inflation balloon (204) through elongate tubular shaft (102) of guide catheter (100) while creating engagement between tactile markers (125, 206, 207). In particular, FIG. 16A shows dilation catheter (220) at a proximal position within elongate tubular shaft (102) of guide catheter (100), with inflation balloon (204) in a deflated state, and with tactile markers (206) proximally positioned in relation to tactile markers (125).

Figure 16B:
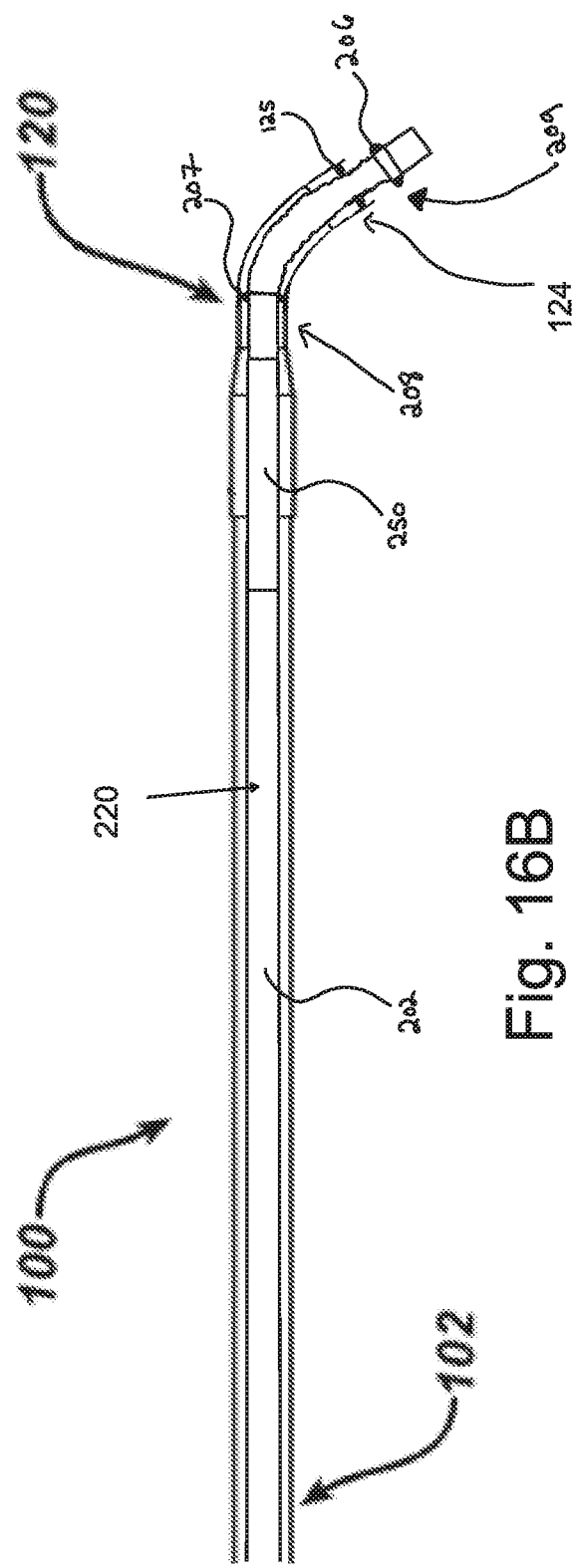
FIG. 16B depicts a side cross-sectional view of the dilation catheter of FIG. 15 disposed in the guide catheter of FIG. 14, with the dilation catheter in an intermediate position, and with the balloon in the non-expanded state.

FIG. 16B shows dilation catheter (220) advanced distally relative to guide catheter (100) to a position where tactile markers (206) and distal end (209) of inflation balloon (204) are distal to distal end (124) of guide catheter (100). Inflation balloon (204) is still in a deflated state. During the transition between the state shown in FIG. 16A and FIG. 16B, tactile markers (206) engaged tactile markers (125), providing a slight and temporary interference that triggered a vibration that was communicated along the lengths of catheters (100, 220). This vibration has thus provided the operator with tactile feedback indicating that distal end (209) of inflation balloon (204) has exited distal end (124) of guide catheter (100), however that inflation is not yet appropriate because proximal end (208) of inflation balloon (204) has yet to exit distal end (124) of guide catheter (100).

Figure 16C:
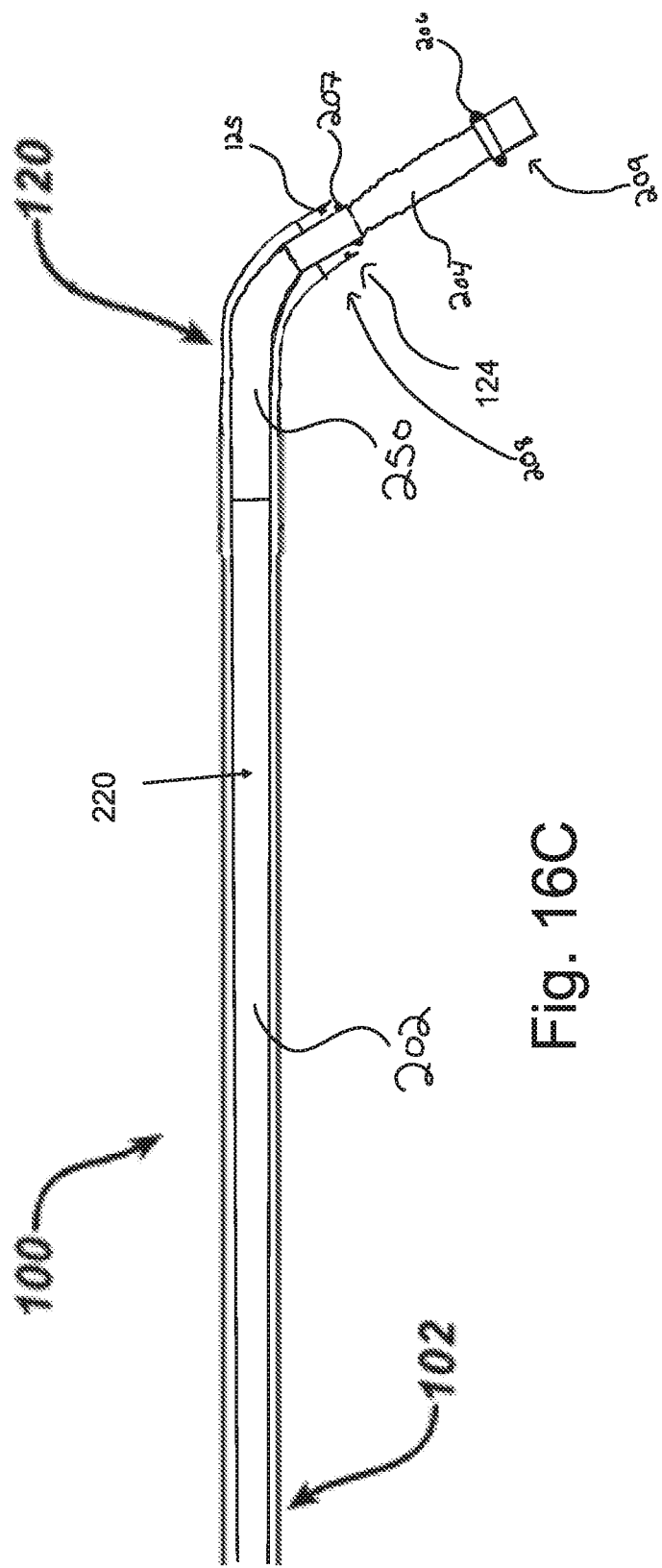
FIG. 16C depicts a side cross-sectional view of the dilation catheter of FIG. 15 disposed in the guide catheter of FIG. 14, with the dilation catheter in a distal position, and with the balloon in the non-expanded state.

FIG. 16C shows dilation catheter (220) advanced distally relative to guide catheter (100) to a position where tactile markers (207) are now distal to distal end (124) of guide catheter (100). Inflation balloon (204) is still in a deflated state. During the transition between the state shown in FIG. 16B and FIG. 16C, tactile markers (207) engaged tactile markers (125), providing a slight and temporary interference that triggered a vibration that was communicated along the lengths of catheters (100, 220). This vibration has thus provided the operator with tactile feedback indicating that the full length of inflation balloon (204) has exited distal end (124) of guide catheter (100). The second tactile response thus indicates to the operator that inflation of inflation balloon (204) is now appropriate because guide catheter (100) will not impede expansion of inflation balloon (204).

Figure 16D:
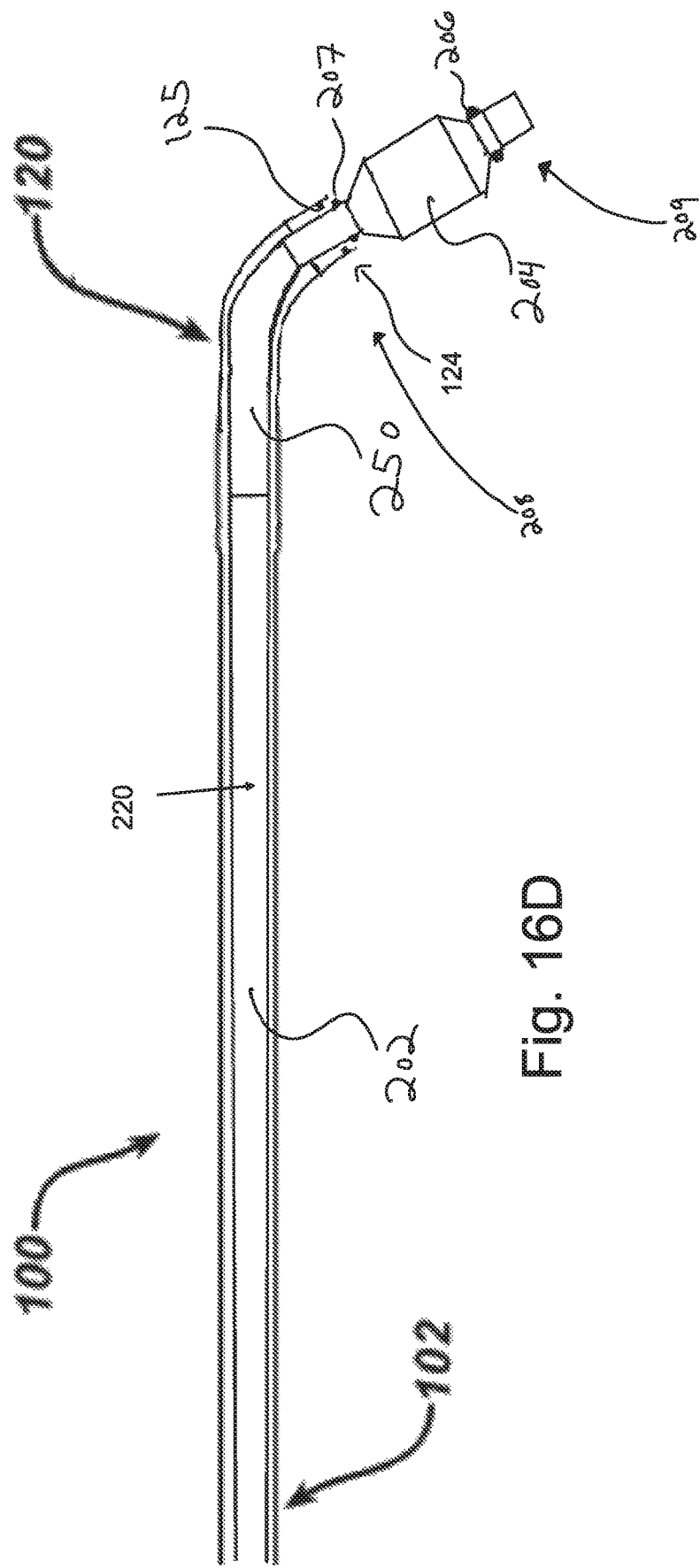
FIG. 16D depicts a side cross-sectional view of the dilation catheter of FIG. 15 disposed in the guide catheter of FIG. 14, with the dilation catheter in a distal position, and with the balloon an expanded state.

FIG. 16D shows inflation balloon (204) in an expanded state. Of course, there may be situations where the operator may wish to advance dilation catheter (220) further distally from guide catheter (100) before expanding inflation balloon (204). In those situations, tactile markers (207) may be relocated further proximally along hollow elongated shaft (202). In some versions, a series of tactile markers (207) are placed at various longitudinal positions along the length of shaft (202). Such longitudinal positions may vary based on the particular location (e.g., sinus ostium) that balloon (204) is intended to reach. For instance, the operator may gauge whether the depth of insertion of dilation catheter (220) is appropriate based on the number of tactile response felt from interactions between tactile markers (125, 207). As another merely illustrative example, tactile markers (207) may be located at certain repeated increments (e.g., every 5 mm, etc.) along the length of shaft (202), allowing the operator to easily calculate the depth of insertion of dilation catheter (220) based on the number of tactile responses felt. Other suitable ways in which tactile markers (125, 206, 207) may be used will be apparent to those of ordinary skill in the art in view of the teachings herein. It should also be understood that tactile markers (206, 207) may be provided on various other instruments that may be passed through guide catheter (100), such that tactile markers (206, 207) need not necessarily be limited to dilation catheter (220).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation apparatus comprising: (a) a hollow elongated shaft comprising: (i) a proximal end, (ii) a first distal end, (iii) a first lumen extending from the proximal end to the first distal end, and (iv) a second lumen extending from the proximal end to a second distal end, wherein the second distal end of the second lumen is proximal in relation to the first distal end; (b) a dilation balloon, wherein the dilation balloon comprises a proximal end and a distal end, wherein the dilation balloon encompasses the second distal end of the second lumen such that the dilation balloon defines an interior in fluid communication with the second lumen; and (c) a standoff member, wherein a distal portion of the standoff member is positioned within the interior of the dilation balloon, wherein the distal portion of the standoff member is distal to the second distal end of the second lumen, wherein the standoff member provides a pathway for fluid communication between the interior of the dilation balloon and the second lumen.

Example 2

The dilation apparatus of Example 1, wherein the first lumen and the second lumen are fluidly isolated from each other.

Example 3

The dilation apparatus of any one or more of Examples 1 through 2, wherein the hollow elongated shaft further comprises a first tube and a second tube.

Example 4

The dilation apparatus of Example 3, wherein the first tube and second tube are fixed to each other.

Example 5

The dilation apparatus of Example 4, wherein the second tube is located within the first tube.

Example 6

The dilation apparatus of Example 5, wherein the proximal end of the dilation balloon is fixed to the first tube, wherein the distal end of dilation balloon is fixed to the second tube.

Example 7

The dilation apparatus of Example 6, wherein the second tube defines the first lumen.

Example 8

The dilation apparatus of Example 7, wherein the first tube has a distal termination that is proximal to a distal termination of the second tube.

Example 9

The dilation apparatus of Example 8, wherein the first tube and the second tube cooperate to define the second lumen.

Example 10

The dilation apparatus of Example 9, wherein the standoff member comprises a proximal end, wherein the proximal end of the standoff member is fixed to either the first tube or the second tube.

Example 11

The dilation apparatus of any one or more of Examples 1 through 10, wherein the first lumen is configured to receive a guidewire.

Example 12

The dilation apparatus of any one or more of Examples 1 through 11, wherein a proximal portion of the standoff member is located within the second lumen.

Example 13

The dilation apparatus of any one or more of Examples 1 through 12, rein the standoff member defines a lumen.

Example 14

The dilation apparatus of any one or more of Examples 1 through 13, wherein the standoff member bisects the second lumen into two equal spaces.

Example 15

The dilation apparatus of any one or more of Examples 1, 2, or 11, wherein the standoff member comprises a collar fitted about an exterior portion of the hollow elongated shaft.

Example 16

The dilation apparatus of any one or more of Examples 1, 2, 11, or 15, wherein a portion of the dilation balloon is bonded to a proximal portion of the standoff member.

Example 17

A catheter system comprising: (a) a guide catheter comprising: (i) a proximal end, (ii) a distal end, (iii) an interior surface, (iv) an exterior surface, and (iii) a first tactile marker extending inwardly from the interior surface, wherein the tactile marker is located closer to the distal end than the proximal end; (b) a working device configured for insertion into the proximal end of the guide catheter and through the distal end of the guide catheter; and (c) a second tactile marker extending outwardly from the working device, wherein the second tactile marker is configured to engage the first tactile marker and thereby provide tactile feedback in response to passage of the second tactile marker past the first tactile marker during longitudinal movement of the working device through the guide catheter.

Example 18

The catheter system of Example 17, wherein the working device comprises a dilation catheter with an expandable dilator, wherein the expandable dilator has a proximal end and a distal end, wherein the second tactile marker is fixed to the proximal end of the expandable dilator.

Example 19

The catheter system of Example 18, further comprising a third tactile marker fixed to the distal end of the expandable dilator.

Example 20

A catheter system comprising: (a) a hollow elongated shaft comprising: (i) a proximal end, (ii) a distal end, (iii) a first lumen having an open distal end, and (iv) a second lumen having an open distal end, wherein the open distal end of the second lumen is proximal in relation to the open distal end of the first lumen; (b) a dilation balloon, wherein the dilation balloon comprises a proximal end and a distal end, wherein the dilation balloon encompasses the open distal end of the second lumen such that the dilation balloon defines an interior in fluid communication with the second lumen; and (c) a support collar fixed to the hollow elongated shaft, wherein the support collar extends past the open end of the second lumen and into the interior of the dilation balloon.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation apparatus comprising:
   (a) a hollow elongated shaft comprising:
      (i) a proximal end,
      (ii) a first distal end,
      (iii) a first lumen extending from the proximal end to the first distal end, and
      (iv) a second lumen extending from the proximal end to a second distal end, wherein the second distal end of the second lumen is proximal in relation to the first distal end;
   (b) a dilation balloon, wherein the dilation balloon comprises a proximal end and a distal end, wherein the dilation balloon encompasses the second distal end of the second lumen such that the dilation balloon defines an interior in fluid communication with the second lumen; and
   (c) a standoff member, wherein a distal portion of the standoff member is positioned within the interior of the dilation balloon, wherein the distal portion of the standoff member is distal to the second distal end of the second lumen, wherein the standoff member is configured to maintain a pathway for fluid communication between the interior of the dilation balloon and the second lumen, wherein the standoff member includes a a collar fitted about an exterior portion of the hollow elongated shaft.

2. The dilation apparatus of claim 1, wherein the first lumen and the second lumen are fluidly isolated from each other.

3. The dilation apparatus of claim 1, wherein the hollow elongated shaft further comprises a first tube and a second tube.

4. The dilation apparatus of claim 3, wherein the first tube and second tube are fixed to each other.

5. The dilation apparatus of claim 4, wherein the second tube is located within the first tube.

6. The dilation apparatus of claim 5, wherein the proximal end of the dilation balloon is fixed to the first tube, wherein the distal end of dilation balloon is fixed to the second tube.

7. The dilation apparatus of claim 6, wherein the second tube defines the first lumen.

8. The dilation apparatus of claim 7, wherein the first tube has a distal termination that is proximal to a distal termination of the second tube.

9. The dilation apparatus of claim 8, wherein the first tube and the second tube cooperate to define the second lumen.

10. The dilation apparatus of claim 9, wherein the standoff member comprises a proximal end, wherein the proximal end of the standoff member is fixed to either the first tube or the second tube.

11. The dilation apparatus of claim 1, wherein the standoff member comprises a filament line.

12. The dilation apparatus of claim 1, wherein a proximal portion of the standoff member is located within the second lumen.

13. The dilation apparatus of claim 1, wherein the standoff member defines a lumen.

14. The dilation apparatus of claim 1, wherein the standoff member bisects the second lumen into two equal spaces.

15. The dilation apparatus of claim 1, wherein a portion of the dilation balloon is bonded to a proximal portion of the standoff member.

16. A catheter system comprising:
   (a) a hollow elongated shaft comprising:
      (i) a proximal end,
      (ii) a distal end,
      (iii) a first lumen having an open distal end, and
      (iv) a second lumen having an open distal end, wherein the open distal end of the second lumen is proximal in relation to the open distal end of the first lumen;
   (b) a dilation balloon, wherein the dilation balloon comprises a proximal end and a distal end, wherein the dilation balloon encompasses the open distal end of the second lumen such that the dilation balloon defines an interior in fluid communication with the second lumen; and
   (c) a tubular member fixed to the hollow elongated shaft, wherein the tubular member extends from a proximal end within the second lumen, and further extends through the open distal end of the second lumen into the interior of the dilation balloon, wherein the tubular member is parallel and offset from the elongate shaft and longitudinally divides a distal portion of the second lumen into a pair of spaces, wherein the pair of spaces extend distally from the proximal end of the tubular member to the open distal end of the second lumen, wherein the tubular member is configured to prevent a collapsed portion of the dilation balloon from occluding the second lumen.

17. The catheter system of claim 16, wherein the tubular member defines a third lumen, wherein the third lumen is configured to provide a third path for fluid communication between the second lumen and the interior of the dilation balloon.

18. The catheter system of claim 16, wherein the tubular member has an open distal end.

19. A catheter system comprising:
(a) a hollow elongated shaft comprising:
   (i) a proximal end,
   (ii) a distal end, and
   (iii) a lumen having an open distal end,
(b) a dilation balloon, wherein the dilation balloon comprises a proximal end and a distal end, wherein the dilation balloon encompasses the open distal end of the lumen such that the dilation balloon defines an interior in fluid communication with the lumen; and
(c) a support member fixed to and surrounding an exterior surface of the hollow elongated shaft, wherein the support member extends from a first end to a second end, wherein the first end is proximal relative to the open distal end of the lumen wherein the second end is distal relative to the open distal end of the lumen and within the interior of the dilation balloon,
wherein the second end of the support member is located outside of the lumen,
wherein an open distal terminal end of the second end of the support member is configured to provide a fluid pathway to inflate the lumen.

\* \* \* \* \*